(12) United States Patent
Hirai et al.

(10) Patent No.: US 6,790,365 B2
(45) Date of Patent: Sep. 14, 2004

(54) PROCESS FOR ADSORBING AND REMOVING ENDOGENOUS CANNABINOID

(75) Inventors: Fumiyasu Hirai, Amagasaki (JP); Tamiji Fujimoto, Settsu (JP); Hiroshi Sakurai, Takasago (JP); Shigeo Furuyoshi, Kobe (JP)

(73) Assignee: Kaneka Corporation, Osaka (JP)

( * ) Notice: Subject to any disclaimer, the term of this patent is extended or adjusted under 35 U.S.C. 154(b) by 0 days.

(21) Appl. No.: 09/961,265

(22) Filed: Sep. 25, 2001

(65) Prior Publication Data

US 2002/0062099 A1 May 23, 2002

(30) Foreign Application Priority Data

Sep. 28, 2000 (JP) ........................................ 2000-296436

(51) Int. Cl.[7] .............................................. B01D 15/00
(52) U.S. Cl. ........................................ 210/690; 210/692
(58) Field of Search ............................... 210/690, 692, 210/282; 502/402

(56) References Cited

U.S. PATENT DOCUMENTS

| | | | |
|---|---|---|---|
| 3,625,652 A | 12/1971 | Fujimoto et al. | ............. 23/230 |
| 3,625,830 A * | 12/1971 | Bergy et al. | ................. 435/128 |
| 3,888,250 A * | 6/1975 | Hill | ............................ 604/6.06 |
| 4,425,237 A * | 1/1984 | Abe et al. | .................... 210/692 |
| 4,640,909 A * | 2/1987 | Ramsden et al. | ............ 502/407 |
| 4,990,458 A | 2/1991 | Rosenfeld | .................... 436/174 |
| 5,015,589 A * | 5/1991 | Ostrea, Jr. | .................... 436/92 |
| 5,062,959 A | 11/1991 | Ross et al. | .................. 210/635 |
| 5,137,626 A * | 8/1992 | Parry et al. | ............... 210/198.2 |
| 6,057,161 A | 5/2000 | Nau | ............................. 436/96 |
| 6,475,478 B2 * | 11/2002 | Hirai et al. | .............. 424/78.12 |

FOREIGN PATENT DOCUMENTS

| | | |
|---|---|---|
| DE | 249274 A1 | 9/1987 |
| EP | 0796865 A2 | 9/1997 |
| EP | 0834350 A1 | 4/1998 |
| EP | 1110602 A1 | 6/2001 |

OTHER PUBLICATIONS

Yin Wang et al, "Polymyxin B binds to anandamide and inhibits its cytotoxic effect"; Fed. European Biochem. Societies; *FEBS Letters* vol. 470, pp. 151–155 (2000) (XP–002181222).

European Search Report dated Nov. 19, 2001.

* cited by examiner

Primary Examiner—Ivars C. Cintins
(74) Attorney, Agent, or Firm—Westerman, Hattori, Daniels & Adrian, LLP

(57) ABSTRACT

There are provided an adsorbent which can effectively adsorb and remove endogenous cannabinoid in fluid, and a process for removing endogenous cannabinoid in fluid by means of the adsorbent. The adsorbent of endogenous cannabinoid comprising an adsorbent for endogenous cannabinoid comprising a water-insoluble material containing a substance whose solubility parameter $\delta$ is at most 12 $((cal/cm^3)^{1/2})$ is obtained. Endogenous cannabinoid in fluid can be effectively adsorbed and removed by contacting the adsorbent of endogenous cannabinoid with fluid containing endogenous cannabinoid.

2 Claims, 1 Drawing Sheet

PROCESS FOR ADSORBING AND REMOVING ENDOGENOUS CANNABINOID

BACKGROUND OF THE INVENTION

The present invention relates to an adsorbent for adsorbing and removing endogenous cannabinoid from body fluid, a process for adsorbing and removing endogenous cannabinoid, and an adsorber for endogenous cannabinoid using the same.

It is known that cannabinoids, the main substance of the physiological action of marijuana (cannabis), brings about mental effects such as hallucination and feeling of euphoria. As cannnabinoid receptors, a receptor (CB1) expressed in central nerves and a receptor (CB2) expressed in peripheral immune cells are known. Endogenous ligands to these cannabinoid receptors, i.e., the ligand generated in living bodies are called endogenous cannabinoid. Known examples of the endogenous cannabinoid are anandamide and 2-arachidonoylglycerol (hereinafter referred to as 2-AG).

The endogenous cannabinoid bears various physiological activities such as (1) drop in blood pressure and bradycardia for cardiovascular system, (2) inhibition of NO generation in macrophages for immune system, (3) defect of memory and inhibition of pain sensation for central nerve system, and (4) induction of endothelial cell apoptosis for coagulation fibrinolysis system.

Recently, it became clear that anandamide is generated in macrophage and 2-AG is generated in blood platelet by means of lipopolysaccharide stimulus (hereinafter referred to as LPS). It is also observed that the generated endogenous cannabinoid causes drop in blood pressure. Furthermore, some raises possibility that the endogenous cannabinoid generated in macrophage or blood platelet is responsible for the blood pressure drop in septic shock. In fact, there is a report that concentrated endogenous cannabinoid was detected in the blood of patients with septic shock.

From these facts, a treatment is expected for the blood pressure drop in septic shock and the like by removing endogenous cannabinoid from body fluid of patients. However, no process for adsorbing and removing endogenous cannabinoid has been available so far. Hence, there has been considerable demand for such process. Yin Wang et al reported that the adsorption of anandamide was possible by means of a substance obtained by fixing an antibiotic, polymyxin B (FEBS Letters, vol. 470, pp151–155, 2000). However, many steps are required in order to prepare such an adsorbent. Besides, the polymyxin B, one of the antibiotics, is very expensive. For these reasons, there is a desire for a process for adsorbing and removing endogenous cannabinoid by using a lower-price substance.

The present invention was carried out in order to solve the above problems. The object of the present invention is to provide an adsorbent which can adsorb and remove endogenous cannabinoid in body fluid efficiently, a process for adsorbing and removing endogenous cannabinoid in body fluid by using the adsorbent, and an adsorber for endogenous cannabinoid.

SUMMARY OF THE INVENTION

Intense studies were conducted as to an adsorbent which can adsorb and remove endogenous cannabinoid in body fluid efficiently. As a result, the present invention has been completed based on the findings that an adsorbent comprising a water-insoluble material containing a substance whose solubility parameter $\delta$ is at most 12 $((cal/cm^3)^{1/2})$ can adsorb and remove endogenous cannabinoid efficiently.

That is, the present invention relates to an adsorbent for endogenous cannabinoid comprising a water-insoluble material containing a substance whose solubility parameter $\delta$ is at most 12 $((cal/cm^3)^{1/2})$.

The water-insoluble material is preferably a styrene-divinyl benzene copolymer.

The endogenous cannabinoid is preferably anandamide.

The endogenous cannabinoid is preferably 2-AG.

The present invention also relates to a process for adsorbing and removing endogenous cannabinoid comprising a step of contacting the adsorbent of endogenous cannabinoid with fluid containing endogenous cannabinoid.

The fluid is body fluid in a preferred embodiment.

The present invention also relates to an adsorber for endogenous cannabinoid comprising a container having a fluid inlet, a fluid outlet and a means for preventing the adsorbent from escaping outside the container, wherein the container is filled with the adsorbent of endogenous cannabinoid.

DETAILED DESCRIPTION

Figure 1:
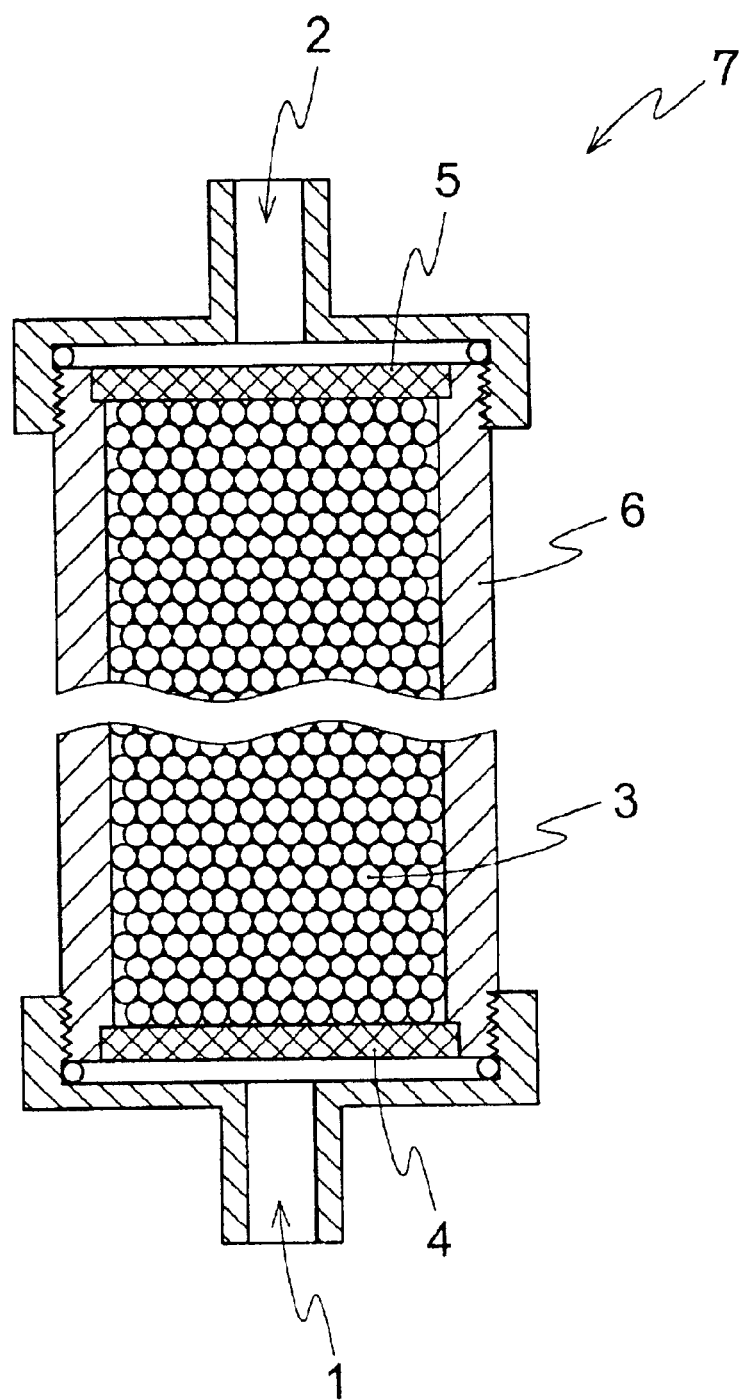
FIG. 1 is a schematic sectional view showing an embodiment of the adsorber of endogenous cannabinoid according to the present invention.

The endogenous cannabinoid in the present invention means endogenous ligands of cannabinoid receptors, i.e., the ligand generated in living bodies. Typical examples of the endogenous cannabinoid are anandamide and 2-AG. Anandamide is represented by the chemical formula $C_{22}H_{37}NO_2$ and has the molecular weight of 347.5. On the other hand, 2-AG is represented by the chemical formula $C_{23}H_{38}O_4$ and has the molecular weight of 378.5.

The body fluid in the present invention means blood, plasma, serum, ascites, lymph, arthral fluid and cerebrospinal fluid, fragments obtainable therefrom and other fluid components derived from living organs.

The adsorbent of the present invention comprises a water-insoluble material containing a substance whose solubility parameter $\delta$ is at most 12 $((cal/cm^3)^{1/2})$, preferably at most 11 $((cal/cm^3)^{1/2})$. When the above solubility parameter $\delta$ is more than 12 $((cal/cm^3)^{1/2})$, endogenous cannabinoid cannot be adsorbed since hydrophilic properties of the substance is increased.

A solubility parameter $\delta$ of a substance is a value defined by $(\Delta E_v/V)^{1/2}$. Herein, $\Delta E_v$ indicates molar evaporation energy of a substance and V indicates molar volume of the substance. $\Delta E_v/V$ indicates molar evaporation energy per unit volume of the substance and is called cohesive energy density. In case of a polymer, cohesive energy density is determined per repeat unit, but when the molecular structure of the repeat unit is definite, solubility parameter $\delta$ can be determined by calculation. The closer solubility parameter $\delta$ of a solute to that of a solvent is, the smaller solubility resistance is. Therefore, solubility parameter $\delta$ serves as an index for solubility. On the other hand, the smaller solubility parameter $\delta$ is, the less polar and the more hydrophobic the substance is. Solubility parameters of various substances are described on pages 675 to 714, VII, *Polymer Handbook*, 4th

*ed.*, edited by J. Brandrup et al. Also, as described in the book, solubility parameter can be determined by experiments when the molecular structure of repeat unit is indefinite as in case of using a commercially available polymer. As a classical approach, there is a process for determining solubility parameters by solvency testing where a target polymer is dissolved in various solvents whose solubility parameters are already known. Also, in case of cross-linked polymers, there is a process for determining solubility parameters from extent of swelling, i.e., a swelling value by immersing a target polymer in various solvents whose solubility parameters are already known. This process is suitable for a styrene-divinyl benzene copolymer and the like. However, the process for determining solubility parameter is not limited thereto.

Examples of the substance whose solubility parameter is at most 12 $((cal/cm^3)^{1/2})$ are polyethylene, polypropylene, poly(methacrylate ester), poly(acrylate ester), poly(vinyl chloride), polystyrene, a styrene-divinyl benzene copolymer, nylon 6, nylon 66, polytetrafluoroethylene, polysulfone, polyurethane and the like, but not limited thereto. Among these, a styrene-divinyl benzene copolymer is preferable.

The water-insoluble material used for the adsorbent of the present invention means a material which is solid at normal temperature under normal pressure and whose solubility to water is extremely small. The water-insoluble carrier is shaped in particles, plates, fibers, hollow fibers and the like, and the shape and the size are not particularly limited. However, when the adsorbent of the present invention is used by filling it in a column, the shape and the size of the adsorbent must be designed to create enough space so that the components contained in materials to be adsorbed such as body fluid other than endogenous cannabinoid can pass through.

For example, when the adsorbent of the present invention is in particles, the average particle size is preferably 5 to 1,000 $\mu$m. When the average particle size is less than 5 $\mu$m, there is a tendency that enough space for passing cannot be formed in case where the body fluid contains cells. When it is more than 1,000 $\mu$m, there is a tendency that no sufficient adsorbing ability per volume can be achieved. The average particle size is more preferably 25 to 1,000 $\mu$m, most preferably 40 to 600 $\mu$m. Narrower particle size distribution is preferable from the viewpoint that increase in pressure drop is not caused. When body fluid is blood, the average particle size of the adsorbent is preferably at least 200 $\mu$m to at most 1,000 $\mu$m.

When the adsorbent of the present invention is fibrous and hollow at the same time, the inner diameter is preferably at least 1 $\mu$m, more preferably 2 to 500 $\mu$m, most preferably 5 to 200 $\mu$m. When the inner diameter is less than 1 $\mu$m, there is a tendency that body fluid does not pass through the hollow sufficiently in case where the body fluid contains cells. When it is more than 500 $\mu$m, there is a tendency that no sufficient adsorbing ability per volume can be achieved.

It is preferable that these water-insoluble materials have numerous pores of suitable size, in other words, a porous structure. The material having a porous structure obviously includes the materials having spaces (macropores) formed by agglomeration of minute spheres when one spherical particle is formed from a basic polymer matrix by the agglomeration. However, there are also materials which have pores formed by agglomeration of nuclei in a minute sphere constituting a basic polymer matrix, and those which have pores (micropores) formed when a copolymer having a three-dimensional structure (polymer net) is swelled by an organic solvent having affinity therewith.

Also, water-insoluble materials having a totally porous structure are more preferable than those having a surface porous structure from the viewpoint of adsorption ability per unit volume of the adsorbent. The pore volume and the specific surface area are preferably large to such a degree that the adsorption property is not lost.

It is preferable that the pore of the water-insoluble porous material has such a size that the target substance of adsorption may enter at a certain probability. Since the adsorptive target of the adsorbent of the present invention, i.e., endogenous cannnabinoid, has relatively small molecular weight of about 300 to 400, water-insoluble materials having a porous structure is quite adequate for endogenous cannnabinoid to enter the pore. Thus, there is no particular limitation for the useful water-insoluble porous material.

In order to improve compatibility with blood and the like, suitable side chain and ligand can be introduced to these materials, or a hydrophilic material can be coated thereto to such a degree that adsorption ability of endogenous cannabinoid is not lost. Examples of the side chain and the ligand are those which have a hydroxyl group or an amino group. Examples of the hydrophilic material are a polymer of hydroxyethyl methacrylate, cellulose and the like, but not limited thereto.

There are various processes for adsorbing and removing endogenous cannabinoid from body fluid by using the adsorbent of the present invention. As the most convenient process, there is one in which body fluid is taken out, stored in a bag and the like, mixed and contacted with an adsorbent to adsorb and remove endogenous cannabinoid, and then the adsorbent is filtered to obtain body fluid from which endogenous cannabinoid is removed. There is also another process in which an adsorbent is filled into a container having an inlet and an outlet for body fluid as well as a filter which passes body fluid but blocks the adsorbent. In the process, the body fluid is then passed through the container and contacted with the adsorbent. Either method can be used, but the latter process is more suitable for the adsorbent of the present invention. This is because the operation is easier and because endogenous cannabinoid can be removed efficiently on-line from body fluid of patients, especially blood, when the device is incorporated into an extracorporeal circulation circuit.

Though the adsorbent of the present invention is used independently in the herein-mentioned extracorporeal circulation circuit, it can be combined with other extracorporeal circulation treatment systems. For example, combination with dialytic treatment is also possible including an artificial dialysis circuit and the like.

Next, explanation is made as to the adsorber of the present invention in which the above adsorbent of endogenous cannabinoid is used based on FIG. 1 showing schematic cross-section of one embodiment. In FIG. 1, numeral 1 indicates inlet of fluid, numeral 2 outlet of fluid, numeral 3 the adsorbent of endogenous cannabinoid of the present invention, numerals 4 and 5 a filter which passes fluid and components included in the fluid but blocks the above adsorbent of endogenous cannabinoid, numeral 6 a column and numeral 7 an adsorber of endogenous cannabinoid. However, an adsorber of endogenous cannabinoid is not limited to these examples. Any adsorber may be used as long as it comprises a container which is filled with the above adsorbent and has a fluid inlet, a fluid outlet, and a means for preventing spillage of the adsorbent of endogenous cannabinoid.

Examples of the means for preventing spillage of the adsorbent are filters such as mesh, non-woven fabric and cotton plug. Though there is no particular limitation for shape, material and size of the container, a cylindrical container is preferable regarding the shape. A material having sterilization resistance is preferable for the container. Examples thereof are silicone-coated glass, polypropylene, poly(vinyl chloride), polycarbonate, polysulfone, polymethylpentene and the like. Preferably, the capacity of the container is 50 to 1,500 ml, and the diameter is 2 to 20 cm. More preferably, the capacity of the container is 100 to 800 ml and the diameter is 3 to 15 cm. Most preferably, the capacity of the container is 150 to 400 ml and the diameter is 4 to 10 cm. When the capacity of the container is less than 50 ml, the adsorbing amount is insufficient. And when it is more than 1,500 ml, the extracorporeal circulation amount increases. Thus, these out-of-ranges are not preferable. The diameter of the container of less than 2 cm is not preferable because pressure drop is increased due to linear velocity growth. The diameter of more than 20 cm is not preferable because handling becomes difficult and yet the risk of coagulation arises due to linear velocity decline.

Hereinafter the present invention is explained in more detail by means of the following Examples, but the present invention is not limited thereto.

EXAMPLE 1

A water-insoluble material (DIAION HP20 available from Mitsubishi Chemical Corporation) comprising a styrene-divinyl benzene copolymer which was a substance having solubility parameter $\delta$ of about 9 $((cal/cm^3)^{1/2})$, was taken in an amount of 0.2 ml. Thereto was added 1.2 ml of 50% ethanol/saline solution in which endogenous cannabinoid, i.e., anandamide (available from Calbiochem-Novabiochem Corporation) was added to adjust the cannabinoid concentration to 0.1 mg/ml. The mixture was shaken at 37° C. for two hours. After shaking, supernatant was removed and washed with saline, and then 1.2 ml of 95% ethanol was added thereto to elute the adsorbed anandamide. By measuring ultraviolet ray absorption of the ethanol-added supernatant at a wavelength of 208 nm, concentration of anandamide was determined, and the amount of adsorption was calculated.

EXAMPLE 2

A water-insoluble material (AMBERLITE XAD-8 available from Organo Corporation) comprising poly (methacrylate ester) which is a substance having solubility parameter $\delta$ of about 9 $((cal/cm^3)^{1/2})$ was used. In the same manner as in Example 1, the material was shaken with anandamide-added 50% ethanol/saline solution to elute the adsorbed anandamide with ethanol, and the amount of adsorption was calculated.

EXAMPLE 3

A water-insoluble material (a hollow fiber material used for PLASMA SEPARATOR SULFLUX, available from Kaneka Corporation) comprising polysulfone which is a substance having solubility parameter $\delta$ of about 10 $((cal/cm^3)^{1/2})$ was used. In the same manner as in Example 1, the material was shaken with anandamide-added 50% ethanol/saline solution to elute the adsorbed anandamide with ethanol, and the amount of adsorption was calculated.

Comparative Example 1

A water-insoluble material (CELLULOFINE GC-200m available from Chisso Corp.) comprising cellulose which is a substance having solubility parameter $\delta$ of about 16 $((cal/cm^3)^{1/2})$ was used. In the same manner as in Example 1, the material was shaken with an anandamide-added 50% ethanol/saline solution to elute the adsorbed anandamide with ethanol, and the amount of adsorption was calculated.

TABLE 1

| | Adsorption amount of anandamide ($\mu$g/ml-adsorbent) | Adsorption ratio (%) |
|---|---|---|
| Ex. No. 1 | 574 | 95.7 |
| Ex. No. 2 | 563 | 93.8 |
| Ex. No. 3 | 422 | 70.3 |
| Com. Ex. No. 1 | 5.5 | 0.9 |

EXAMPLE 4

A water-insoluble material (DIAION HP20 available from Mitsubishi Chemical Corporation) comprising a styrene-divinyl benzene copolymer which is a substance having solubility parameter $\delta$ of about 9 $((cal/cm^3)^{1/2})$, was taken in an amount of 0.2 ml. Thereto was added 1.2 ml of 50% ethanol/saline solution in which endogenous cannabinoid, i.e., 2-AG (available from Calbiochem-Novabiochem Corporation) was added to adjust the cannabinoid concentration to 0.1 mg/ml. The mixture was shaken at 37° C. for two hours. After shaking, supernatant was removed and washed with saline, and then 1.2 ml of 95% ethanol was added thereto to elute the adsorbed 2-AG. By measuring ultraviolet ray absorption of the ethanol-added supernatant at a wavelength of 208 nm, concentration of 2-AG was determined, and the amount of adsorption was calculated.

EXAMPLE 5

A water-insoluble material (AMBERLITE XAD-8 available from Organo Corporation) comprising poly (methacrylate ester) which is a substance having solubility parameter $\delta$ of about 9 $((cal/cm^3)^{1/2})$ was used. In the same manner as in Example 4, the material was shaken with human 2-AG added 50% ethanol/saline solution to elute the adsorbed 2-AG with ethanol, and the amount of adsorption was calculated.

EXAMPLE 6

A water-insoluble material (a hollow fiber material used for PLASMA SEPARATOR SULFLUX, available from Kaneka Corporation) comprising polysulfone which is a substance having solubility parameter $\delta$ of about 10 $((cal/cm^3)^{1/2})$ was used. In the same manner as in Example 4, the material was shaken with human 2-AG added 50% ethanol/saline solution to elute the adsorbed 2-AG with ethanol, and the amount of adsorption was calculated.

Comparative Example 2

A water-insoluble material (CELLULOFINE GC-200m available from Chisso Corp.) comprising cellulose which is a substance having solubility parameter $\delta$ of about 16 $((cal/cm^3)^{1/2})$ was used. In the same manner as in Example 4, the material was shaken with human 2-AG added 50% ethanol/saline solution to elute the adsorbed 2-AG with ethanol, and the amount of adsorption was calculated.

TABLE 2

|  | Adsorption amount of 2-AG ($\mu$g/ml-adsorbent) | Adsorption ratio (%) |
| --- | --- | --- |
| Ex. No. 4 | 127 | 21.2 |
| Ex. No. 5 | 109 | 18.2 |
| Ex. No. 6 | 61.2 | 10.2 |
| Com. Ex. No. 2 | 10.4 | 1.7 |

By using the adsorbent for endogenous cannabinoid of the present invention comprising a water-insoluble material containing a substance whose solubility parameter $\delta$ is at most 12 $((cal/cm^3)^{1/2})$, it is possible to adsorb and remove endogenous cannabinoid effectively.

What is claimed is:

1. A process for adsorbing and removing endogenous anandamide or endogenous 2-arachidonoylglycerol comprising a step of contacting an adsorbent for endogenous anandamide or endogenous 2-arachidonoylglycerol comprising a water-insoluble material containing a substance whose solubility parameter $\delta$ is at most 12 $((cal/cm^3)^{1/2})$ with fluid containing endogenous anandamide or endogenous 2-arachidonoylglycerol, wherein the substance whose solubility parameter $\delta$ is at most 12 $((cal/cm^3)^{1/2})$ is at least one substance selected from the group consisting of polyethylene, polypropylene, poly(methacrylate ester), poly(acrylate ester), poly (vinyl chloride), polystyrene, a styrene-divinyl benzene copolymer, nylon 6, nylon 66, polytetrafluoroethylene, polysulfone and polyurethane;

wherein said fluid is a body fluid selected from the group consisting of blood, plasma, serum, ascites, lymph, arthral fluid, cerebrospinal fluid and fragments obtained therefrom.

2. A process for cleansing endogenous anandamide or endogenous 2-arachidonoylglycerol from a body fluid, comprising the steps of:

providing an adsorbent for endogenous anandamide or endogenous 2-arachidonoylglycerol comprising a water-insoluble material containing a substance whose solubility parameter $\delta$ is at most 12 $((cal/cm^3)^{1/2})$;

removing body fluid from a living body, wherein the fluid is a body fluid selected from the group consisting of blood, plasma, serum, ascites, lymph, arthral fluid, cerebrospinal fluid and fragments obtained therefrom, and wherein the fluid contains endogenous anandamide or endogenous 2-arachidonoylglycerol;

contacting said adsorbent with said body fluid, thereby reducing the amount of endogenous anandamide or endogenous 2-arachidonoylglycerol in the fluid; and returning said body fluid containing a reduced amount of endogenous anandamide or endogenous 2-arachidonoylglycerol to said body.

* * * * *